(12) United States Patent
Singh et al.

(10) Patent No.: US 9,717,527 B2
(45) Date of Patent: Aug. 1, 2017

(54) EXTERNAL FIXATOR SYSTEM

(71) Applicant: Stryker European Holdings I, LLC, Kalamazoo, MI (US)

(72) Inventors: Manoj Kumar Singh, Mahwah, NJ (US); Yves Stephane Crozet, Ramsey, NJ (US); Vinzenz Andreas Burgherr, Bern (CH); Mark Thomas Dahl, Afton, MN (US)

(73) Assignee: Stryker European Holdings I, LLC, Kalamazoo, MI (US)

( * ) Notice: Subject to any disclaimer, the term of this patent is extended or adjusted under 35 U.S.C. 154(b) by 0 days.

(21) Appl. No.: 14/456,121

(22) Filed: Aug. 11, 2014

(65) Prior Publication Data

US 2014/0350557 A1 Nov. 27, 2014

Related U.S. Application Data

(63) Continuation of application No. 13/206,058, filed on Aug. 9, 2011, now Pat. No. 8,834,467.

(30) Foreign Application Priority Data

Aug. 11, 2010 (EP) .................................... 10172523
Aug. 4, 2011 (EP) .................................... 11176512

(51) Int. Cl.
*A61B 17/00* (2006.01)
*A61B 17/60* (2006.01)
(Continued)

(52) U.S. Cl.
CPC .............. *A61B 17/60* (2013.01); *A61B 17/62* (2013.01); *A61B 17/66* (2013.01); *A61B 17/8875* (2013.01)

(58) Field of Classification Search
CPC ..... A61B 17/60–17/666; Y10T 403/70; Y10T 403/7062–403/7067
See application file for complete search history.

(56) References Cited

U.S. PATENT DOCUMENTS

| 6,214 A | 3/1849 | Yerger |
|---|---|---|
| 2,055,024 A | 9/1936 | Bittner |

(Continued)

FOREIGN PATENT DOCUMENTS

| CH | 596826 A5 | 3/1978 |
|---|---|---|
| DE | 3114455 A1 | 10/1982 |

(Continued)

OTHER PUBLICATIONS

Extended European Search Report for Application No. EP14154811 dated Jun. 30, 2014.

(Continued)

*Primary Examiner* — Jan Christopher Merene
*Assistant Examiner* — Steven Cotroneo
(74) *Attorney, Agent, or Firm* — Lerner, David, Littenberg, Krumholz & Mentlik, LLP (57) ABSTRACT

An external fixator system comprising at least two fixation plates which are arranged at a distance to each another, at least one adjustable length strut having a first end region and a second end region which are in connection with the fixation plates and at least one actuation unit to adjust the length of the strut in order to adjust the distance and/or orientation between the fixation plates. The actuation unit is in a fixed connection with at least one of the fixation plates as well as with at least one of the end regions of the respective strut in order to connect the strut with the fixation plate. The actuation unit comprises a feedback unit which provides the user with a feedback concerning the degree of the actuation.

19 Claims, 4 Drawing Sheets

(51) Int. Cl.
    *A61B 17/62*     (2006.01)
    *A61B 17/66*     (2006.01)
    *A61B 17/88*     (2006.01)

(56) References Cited

U.S. PATENT DOCUMENTS

| | | | |
|---|---|---|---|
| 2,291,747 | A | 8/1942 | Neuwirth |
| 2,333,033 | A | 10/1943 | Mraz |
| 2,391,537 | A | 12/1945 | Anderson |
| 2,393,831 | A | 1/1946 | Stader |
| 2,406,987 | A | 9/1946 | Anderson |
| 2,883,219 | A | 4/1959 | Cox |
| 3,691,788 | A | 9/1972 | Mazziotti |
| 3,727,610 | A | 4/1973 | Riniker |
| 3,863,037 | A | 1/1975 | Schindler et al. |
| 3,941,123 | A | 3/1976 | Volkov et al. |
| 3,977,397 | A | 8/1976 | Kalnberz et al. |
| 3,985,127 | A | 10/1976 | Volkov et al. |
| 4,006,740 | A | 2/1977 | Volkov et al. |
| 4,100,919 | A | 7/1978 | Oganesyan et al. |
| 4,127,119 | A * | 11/1978 | Kronner .................. A61B 17/62 606/56 |
| 4,185,623 | A | 1/1980 | Volkov et al. |
| 4,308,863 | A | 1/1982 | Fischer |
| 4,338,927 | A | 7/1982 | Volkov et al. |
| 4,365,624 | A | 12/1982 | Jaquet |
| 4,403,606 | A | 9/1983 | Woo et al. |
| 4,450,834 | A | 5/1984 | Fischer |
| 4,520,983 | A | 6/1985 | Templeman |
| 4,554,915 | A | 11/1985 | Brumfield |
| 4,611,586 | A | 9/1986 | Agee et al. |
| 4,615,338 | A | 10/1986 | Ilizarov et al. |
| 4,730,608 | A | 3/1988 | Schlein |
| 4,768,524 | A | 9/1988 | Hardy |
| 4,784,125 | A | 11/1988 | Monticelli et al. |
| 4,819,496 | A | 4/1989 | Shelef |
| 4,889,111 | A | 12/1989 | Ben-Dov |
| 4,976,582 | A | 12/1990 | Clavel et al. |
| 4,978,348 | A | 12/1990 | Ilizarov et al. |
| 5,028,180 | A | 7/1991 | Sheldon et al. |
| 5,062,844 | A | 11/1991 | Jamison et al. |
| 5,074,866 | A | 12/1991 | Sherman et al. |
| 5,087,258 | A | 2/1992 | Schewior |
| 5,112,331 | A | 5/1992 | Miletich |
| 5,122,140 | A | 6/1992 | Asche et al. |
| 5,179,525 | A | 1/1993 | Griffis et al. |
| 5,207,676 | A | 5/1993 | Canadell et al. |
| 5,275,598 | A | 1/1994 | Cook |
| 5,279,176 | A | 1/1994 | Tahmasebi et al. |
| 5,301,566 | A | 4/1994 | Tahmasebi et al. |
| 5,353,504 | A | 10/1994 | Pai |
| 5,358,504 | A | 10/1994 | Paley et al. |
| 5,372,597 | A | 12/1994 | Hotchkiss et al. |
| 5,397,322 | A | 3/1995 | Campopiano et al. |
| 5,437,666 | A | 8/1995 | Tepic et al. |
| 5,451,225 | A | 9/1995 | Ross, Jr. et al. |
| 5,466,237 | A | 11/1995 | Byrd, III et al. |
| 5,496,319 | A | 3/1996 | Allard et al. |
| 5,540,686 | A | 7/1996 | Zippel et al. |
| 5,568,993 | A | 10/1996 | Potzick |
| 5,630,814 | A | 5/1997 | Ross, Jr. et al. |
| 5,658,283 | A | 8/1997 | Huebner |
| 5,662,648 | A | 9/1997 | Faccioli et al. |
| 5,681,309 | A | 10/1997 | Ross, Jr. et al. |
| 5,688,271 | A | 11/1997 | Faccioli et al. |
| 5,702,389 | A | 12/1997 | Taylor et al. |
| 5,709,681 | A | 1/1998 | Pennig |
| 5,713,897 | A | 2/1998 | Goble et al. |
| 5,725,526 | A | 3/1998 | Allard et al. |
| 5,725,527 | A | 3/1998 | Biedermann et al. |
| 5,728,095 | A | 3/1998 | Taylor et al. |
| 5,766,173 | A | 6/1998 | Ross, Jr. et al. |
| 5,776,132 | A | 7/1998 | Blyakher |
| 5,776,173 | A | 7/1998 | Madsen, Jr. et al. |
| 5,788,695 | A | 8/1998 | Richardson |
| 5,797,908 | A | 8/1998 | Meyers et al. |
| 5,843,081 | A | 12/1998 | Richardson |
| 5,846,245 | A | 12/1998 | McCarthy et al. |
| 5,863,292 | A | 1/1999 | Tosic |
| 5,870,834 | A | 2/1999 | Sheldon |
| 5,885,282 | A | 3/1999 | Szabo |
| 5,891,143 | A | 4/1999 | Taylor et al. |
| 5,897,555 | A | 4/1999 | Clyburn et al. |
| 5,919,192 | A | 7/1999 | Shouts |
| 5,921,985 | A | 7/1999 | Ross, Jr. et al. |
| 5,928,230 | A | 7/1999 | Tosic |
| 5,931,837 | A | 8/1999 | Marsh et al. |
| 5,968,043 | A * | 10/1999 | Ross et al. .................. 606/56 |
| 5,971,984 | A | 10/1999 | Taylor et al. |
| 5,976,133 | A | 11/1999 | Kraus et al. |
| 5,997,537 | A | 12/1999 | Walulik |
| 6,007,535 | A | 12/1999 | Rayhack et al. |
| 6,010,501 | A | 1/2000 | Raskin et al. |
| 6,021,579 | A | 2/2000 | Schimmels et al. |
| 6,030,386 | A * | 2/2000 | Taylor .................. A61B 17/62 606/54 |
| 6,036,691 | A | 3/2000 | Richardson |
| 6,086,283 | A | 7/2000 | Ziegert |
| 6,090,111 | A | 7/2000 | Nichols |
| 6,099,217 | A | 8/2000 | Wiegand et al. |
| 6,129,727 | A | 10/2000 | Austin et al. |
| 6,176,860 | B1 | 1/2001 | Howard |
| 6,196,081 | B1 | 3/2001 | Yau |
| 6,245,071 | B1 | 6/2001 | Pierson |
| 6,277,118 | B1 | 8/2001 | Grant et al. |
| 6,328,737 | B1 | 12/2001 | Moorcroft et al. |
| 6,342,052 | B1 | 1/2002 | Allende |
| 6,342,054 | B1 | 1/2002 | Mata |
| 6,355,037 | B1 | 3/2002 | Crosslin et al. |
| 6,371,957 | B1 | 4/2002 | Amrein et al. |
| 6,391,250 | B1 | 5/2002 | Wolfsgruber et al. |
| 6,423,061 | B1 | 7/2002 | Bryant |
| 6,428,540 | B1 | 8/2002 | Claes et al. |
| 6,537,275 | B2 | 3/2003 | Venturini et al. |
| 6,565,565 | B1 | 5/2003 | Yuan et al. |
| 6,565,567 | B1 | 5/2003 | Haider |
| 6,610,063 | B2 | 8/2003 | Kumar et al. |
| 6,613,049 | B2 | 9/2003 | Winquist et al. |
| 6,648,583 | B1 | 11/2003 | Roy et al. |
| 6,648,891 | B2 | 11/2003 | Kim |
| 6,652,524 | B1 | 11/2003 | Weiner |
| 6,671,975 | B2 | 1/2004 | Hennessey |
| 6,701,174 | B1 | 3/2004 | Krause et al. |
| 6,733,502 | B2 | 5/2004 | Altarac et al. |
| 6,746,448 | B2 | 6/2004 | Weiner et al. |
| 6,769,194 | B2 | 8/2004 | Hennessey |
| 6,784,125 | B1 | 8/2004 | Yamakawa et al. |
| 6,793,655 | B2 | 9/2004 | Orsak |
| 6,860,883 | B2 | 3/2005 | Janowski et al. |
| 6,964,663 | B2 | 11/2005 | Grant et al. |
| 7,022,122 | B2 | 4/2006 | Amreim et al. |
| 7,048,735 | B2 | 5/2006 | Ferrante et al. |
| 7,127,660 | B2 | 10/2006 | Blaum |
| 7,147,640 | B2 | 12/2006 | Huebner et al. |
| 7,197,806 | B2 | 4/2007 | Boudreaux et al. |
| 7,226,449 | B2 | 6/2007 | Venturini et al. |
| 7,261,713 | B2 | 8/2007 | Langmaid et al. |
| 7,276,069 | B2 | 10/2007 | Biedermann et al. |
| 7,282,052 | B2 | 10/2007 | Mullaney |
| 7,291,148 | B2 | 11/2007 | Agee et al. |
| 7,306,601 | B2 | 12/2007 | McGrath et al. |
| 7,311,711 | B2 | 12/2007 | Cole |
| 7,361,176 | B2 | 4/2008 | Cooper et al. |
| 7,377,923 | B2 | 5/2008 | Purcell et al. |
| 7,422,593 | B2 * | 9/2008 | Cresina et al. .................. 606/54 |
| 7,449,023 | B2 | 11/2008 | Walulik et al. |
| 7,468,063 | B2 | 12/2008 | Walulik et al. |
| 7,479,142 | B2 | 1/2009 | Weiner et al. |
| 7,491,008 | B2 | 2/2009 | Thomke et al. |
| 7,507,240 | B2 | 3/2009 | Olsen |
| 7,527,626 | B2 | 5/2009 | Lutz et al. |
| 7,575,575 | B2 | 8/2009 | Olsen et al. |
| 7,578,822 | B2 | 8/2009 | Rezach et al. |
| RE40,914 | E | 9/2009 | Taylor et al. |

(56) References Cited

U.S. PATENT DOCUMENTS

| | | |
|---|---|---|
| 7,608,074 B2 | 10/2009 | Austin et al. |
| 7,632,271 B2 | 12/2009 | Baumgartner et al. |
| 7,699,848 B2 | 4/2010 | Hoffman et al. |
| 7,708,736 B2 | 5/2010 | Mullaney |
| 7,749,224 B2 | 7/2010 | Cresina et al. |
| 7,763,020 B2 | 7/2010 | Draper |
| 7,806,843 B2 | 10/2010 | Marin |
| 7,815,586 B2 | 10/2010 | Grant et al. |
| 7,875,030 B2 | 1/2011 | Hoffmann-Clair et al. |
| 7,881,771 B2 | 2/2011 | Koo et al. |
| 7,887,498 B2 | 2/2011 | Marin |
| 7,887,537 B2 | 2/2011 | Ferrante et al. |
| 7,931,650 B2 | 4/2011 | Winquist et al. |
| 7,938,829 B2 | 5/2011 | Mullaney |
| 7,955,333 B2 | 6/2011 | Yeager |
| 7,955,334 B2 | 6/2011 | Steiner et al. |
| 7,985,221 B2 | 7/2011 | Coull et al. |
| 8,029,505 B2 | 10/2011 | Hearn et al. |
| 8,057,474 B2 | 11/2011 | Knuchel et al. |
| 8,114,077 B2 | 2/2012 | Steiner et al. |
| 8,137,347 B2 | 3/2012 | Weiner et al. |
| 8,142,432 B2 | 3/2012 | Matityahu |
| 8,147,490 B2 | 4/2012 | Bauer |
| 8,147,491 B2 | 4/2012 | Lavi |
| 8,157,800 B2 | 4/2012 | Vvedensky et al. |
| 8,172,849 B2 | 5/2012 | Noon et al. |
| 8,182,483 B2 | 5/2012 | Bagnasco et al. |
| 8,187,274 B2 | 5/2012 | Schulze |
| 8,192,434 B2 | 6/2012 | Huebner et al. |
| 8,202,273 B2 | 6/2012 | Karidis |
| 8,241,285 B2 | 8/2012 | Mullaney |
| 8,251,937 B2 | 8/2012 | Marin |
| 8,257,353 B2 | 9/2012 | Wong et al. |
| 8,282,652 B2 | 10/2012 | Mackenzi et al. |
| 8,858,555 B2 | 10/2014 | Crozet et al. |
| 8,906,020 B2 | 12/2014 | Crozet et al. |
| 2001/0025181 A1 | 9/2001 | Freedlan |
| 2001/0049526 A1 | 12/2001 | Venturini et al. |
| 2002/0010465 A1 | 1/2002 | Koo et al. |
| 2002/0013584 A1 | 1/2002 | Termaten |
| 2002/0042613 A1 | 4/2002 | Mata |
| 2002/0165543 A1 | 11/2002 | Winquist et al. |
| 2003/0063949 A1 | 4/2003 | Hohenocker |
| 2003/0069580 A1 | 4/2003 | Langmaid et al. |
| 2003/0106230 A1 | 6/2003 | Hennessey |
| 2003/0109879 A1 | 6/2003 | Orsak |
| 2003/0181911 A1 | 9/2003 | Venturini |
| 2003/0191466 A1 | 10/2003 | Austin et al. |
| 2003/0216734 A1 | 11/2003 | Mingozzi et al. |
| 2003/0225406 A1 | 12/2003 | Weiner et al. |
| 2004/0059331 A1 | 3/2004 | Mullaney |
| 2004/0073211 A1 | 4/2004 | Austin et al. |
| 2004/0073212 A1 | 4/2004 | Kim |
| 2004/0097944 A1 | 5/2004 | Koman et al. |
| 2004/0116926 A1 | 6/2004 | Venturini et al. |
| 2004/0133199 A1 | 7/2004 | Coati et al. |
| 2004/0133200 A1 | 7/2004 | Ruch et al. |
| 2004/0167518 A1 | 8/2004 | Estrada, Jr. |
| 2005/0015087 A1 | 1/2005 | Walulik et al. |
| 2005/0043730 A1 | 2/2005 | Janowski et al. |
| 2005/0059968 A1 | 3/2005 | Grant et al. |
| 2005/0084325 A1 | 4/2005 | O'Brien et al. |
| 2005/0113829 A1 | 5/2005 | Walulik et al. |
| 2005/0119656 A1 | 6/2005 | Ferrante et al. |
| 2005/0149018 A1 | 7/2005 | Cooper et al. |
| 2005/0215997 A1 | 9/2005 | Austin et al. |
| 2005/0234448 A1 | 10/2005 | McCarthy |
| 2005/0248156 A1 | 11/2005 | Hsieh |
| 2005/0251136 A1 | 11/2005 | Noon et al. |
| 2006/0155276 A1 | 7/2006 | Walulik et al. |
| 2006/0184169 A1 | 8/2006 | Stevens |
| 2006/0229605 A1 | 10/2006 | Olsen |
| 2006/0235383 A1 | 10/2006 | Hollawell |
| 2006/0243873 A1 | 11/2006 | Carnevali |
| 2006/0247622 A1 | 11/2006 | Maughan et al. |
| 2006/0247629 A1 | 11/2006 | Maughan et al. |
| 2006/0261221 A1 | 11/2006 | Carnevali |
| 2006/0276786 A1 | 12/2006 | Brinker |
| 2006/0287652 A1 | 12/2006 | Lessig et al. |
| 2007/0038217 A1 | 2/2007 | Brown et al. |
| 2007/0043354 A1 | 2/2007 | Koo et al. |
| 2007/0049930 A1* | 3/2007 | Hearn et al. ................ 606/56 |
| 2007/0055234 A1 | 3/2007 | McGrath et al. |
| 2007/0123857 A1 | 5/2007 | Deffenbaugh et al. |
| 2007/0161983 A1 | 7/2007 | Cresina et al. |
| 2007/0161984 A1 | 7/2007 | Cresina et al. |
| 2007/0162022 A1 | 7/2007 | Zhang et al. |
| 2007/0225704 A1 | 9/2007 | Ziran et al. |
| 2007/0233061 A1 | 10/2007 | Lehmann et al. |
| 2007/0250071 A1 | 10/2007 | Soerensen et al. |
| 2007/0255280 A1 | 11/2007 | Austin et al. |
| 2007/0282338 A1 | 12/2007 | Mullaney |
| 2008/0021451 A1 | 1/2008 | Coull et al. |
| 2008/0228185 A1 | 9/2008 | Vasta et al. |
| 2008/0269741 A1* | 10/2008 | Karidis ................ A61B 17/62 606/56 |
| 2009/0018541 A1 | 1/2009 | Lavi |
| 2009/0036890 A1 | 2/2009 | Karidis |
| 2009/0036891 A1 | 2/2009 | Brown et al. |
| 2009/0105621 A1 | 4/2009 | Boyd et al. |
| 2009/0131935 A1 | 5/2009 | Yeager |
| 2009/0177198 A1 | 7/2009 | Theodoros et al. |
| 2009/0198234 A1* | 8/2009 | Knuchel ................ A61B 17/62 606/56 |
| 2009/0198235 A1* | 8/2009 | Steiner et al. ................ 606/57 |
| 2009/0264883 A1 | 10/2009 | Steiner et al. |
| 2009/0287212 A1 | 11/2009 | Hirata et al. |
| 2009/0312757 A1 | 12/2009 | Kehres et al. |
| 2010/0087819 A1 | 4/2010 | Mullaney |
| 2010/0145336 A1 | 6/2010 | Draper |
| 2010/0179548 A1 | 7/2010 | Marin |
| 2010/0191239 A1 | 7/2010 | Sakkers et al. |
| 2010/0234844 A1 | 9/2010 | Edelhauser et al. |
| 2010/0249779 A1 | 9/2010 | Hotchkiss et al. |
| 2010/0280516 A1 | 11/2010 | Taylor |
| 2010/0298827 A1 | 11/2010 | Cremer et al. |
| 2010/0305568 A1 | 12/2010 | Ross et al. |
| 2010/0312243 A1 | 12/2010 | Ross et al. |
| 2010/0331840 A1 | 12/2010 | Ross et al. |
| 2011/0060336 A1 | 3/2011 | Pool et al. |
| 2011/0066151 A1 | 3/2011 | Murner et al. |
| 2011/0082458 A1 | 4/2011 | Crozet et al. |
| 2011/0098707 A1 | 4/2011 | Mullaney |
| 2011/0112533 A1 | 5/2011 | Venturini et al. |
| 2011/0118737 A1 | 5/2011 | Vasta et al. |
| 2011/0118738 A1 | 5/2011 | Vasta et al. |
| 2011/0172663 A1 | 7/2011 | Mullaney |
| 2011/0172664 A1 | 7/2011 | Bagnasco et al. |
| 2011/0245830 A1 | 10/2011 | Zgonis et al. |
| 2011/0313418 A1 | 12/2011 | Nikonovas |
| 2011/0313419 A1* | 12/2011 | Mullaney ................ 606/56 |
| 2012/0004659 A1 | 1/2012 | Miller et al. |
| 2012/0041439 A1 | 2/2012 | Singh et al. |
| 2012/0078251 A1 | 3/2012 | Benenati et al. |
| 2012/0089142 A1 | 4/2012 | Mullaney et al. |
| 2012/0095462 A1 | 4/2012 | Miller |
| 2012/0136355 A1 | 5/2012 | Wolfson |
| 2012/0143190 A1 | 6/2012 | Wolfson |

FOREIGN PATENT DOCUMENTS

| | | |
|---|---|---|
| DE | 4421223 A1 | 12/1995 |
| DE | 202006006734 U1 | 6/2006 |
| EP | 0377744 A1 | 7/1990 |
| EP | 611007 A1 | 8/1994 |
| EP | 1016381 A1 | 7/2000 |
| EP | 1136041 A2 | 9/2001 |
| EP | 2417923 A1 | 2/2012 |
| EP | 2417924 A1 | 2/2012 |
| FR | 2439002 A1 | 5/1980 |
| FR | 2576774 A1 | 8/1986 |
| FR | 2756025 A1 | 5/1998 |
| GB | 2250682 A | 6/1992 |
| IT | 1259768 B | 3/1996 |

(56) References Cited

FOREIGN PATENT DOCUMENTS

| WO | 92/14426 | 9/1992 |
|---|---|---|
| WO | 9418898 | 9/1994 |
| WO | 97/30650 | 8/1997 |
| WO | 97/30651 | 8/1997 |
| WO | 01/15611 A1 | 3/2001 |
| WO | 01/22892 A1 | 4/2001 |
| WO | 01/78613 | 10/2001 |
| WO | 03/086213 | 10/2003 |
| WO | 2006116307 | 11/2006 |
| WO | 2007067297 A2 | 6/2007 |
| WO | 2007075114 | 7/2007 |
| WO | 2007/111576 A2 | 10/2007 |
| WO | 2010104567 A1 | 9/2010 |
| WO | 2012102685 A1 | 8/2012 |

OTHER PUBLICATIONS

Extended European Search Report for Application No. EP14158464 dated Jul. 3, 2014.
Basic Ilizarov Techniques, Techniques in Orthopaedics, vol. 5, No. 4, pp. 55-59, Dec. 1990.
S.V. Sreenivasan et al., "Closed-Form Direct Displacement Analysis of a 6-6 Stewart Platform," Mech. Mach. Theory, vol. 29, No. 6, pp. 855-864, 1994.
Tsai, Technical Research Report, The Jacobian Analysis of a Parallel Manipulator Using Reciprocal Screws, T.R. 98-34.
Hwang et al., Asian Journal of Control, vol. 6, No. 1, pp. 136-144, Mar. 2004.
U.S. Appl. No. 09/827,252 (not yet published).
European Search Report, EP 08 15 0960 dated Jul. 30, 2008.
Smith&Nephew, Taylor Spatial Frame, website printout, Aug. 12, 2009.
Alizade et al., Mech. Mach. Theory, vol. 29, No. 1, pp. 115-124, 1994, Great Britain, © 1993.
International Search Report and Written Opinion, PCT/US2010/000712, dated Jun. 28, 2010.
European Search Report, EP 08 15 7614 dated Aug. 21, 2008.
European Search Report, EP 08 15 4754 dated Jul. 4, 2008.
European Search Report, EP 08 15 0944 dated Aug. 18, 2008.
BIOMET® Vision™ Footring™ System: Surgical Technique, 39 pages, (2008).
European Search Report, EP 10 172 523 dated Mar. 25, 2011.
European Search Report, EP 11176512, dated Sep. 19, 2011.
European Search Report, EP 11176566, dated Sep. 20, 2011.
Nanua et al., IEEE Transactions on Robotics and Automation, vol. 6, No. 4, pp. 438-444, Aug. 1990.
Partial European Search Report for Application No. EP13180720 dated Dec. 3, 2013.
European Search Report for Application No. EP15167691 dated Sep. 17, 2015.
Tibiotalocalcaneal Arthrodesis with the Ilizarov method, Surgical Technique, Ilizarov Foot and Ankle External Fixation, Smith & Nephew, Inc., May 2010.

* cited by examiner

EXTERNAL FIXATOR SYSTEM

CROSS-REFERENCE TO RELATED APPLICATIONS

The present application is a continuation of U.S. patent application Ser. No. 13/206,058, filed Aug. 9, 2011, and is related to European Application No. 10 172 523.2 filed Aug. 11, 2010, and European Application No. 11 176 512.9 filed on Aug. 4, 2011, the disclosures of which are hereby incorporated herein by reference.

FIELD OF THE INVENTION

The present invention relates to manipulating the position of two or more fixation plates of an external fixator system, and more particularly, to manipulating the position of two or more fixation plates with respect to one another by actuating an adjustment member or actuation unit located in a user-friendly position wherein the actuation of the adjustment member also provides feedback to the user.

BACKGROUND OF THE INVENTION

Many different types of bone deformities can be corrected using external fixation systems to perform the distraction osteogenesis process. For example, an Ilizarov device or similar external fixation system may be used. Such systems generally use rings also designated as fixation plates connected by threaded rods or struts with nuts for manipulation, angulation, and translation of the length discrepancies of bones. The nuts that are used to adjust the length of the struts are generally manually adjusted by the patient with a wrench or by hand to change the positions of the rings and/or percutaneous fixation components.

As the position adjustments of the components are made where the nuts are secured, it can be difficult for the patient to make the required daily adjustments with consideration of stable fixation in mind. Other devices use different techniques to adjust the effective length of the struts or rods but all must be adjusted somewhere between the ends thereof. The devices generally offer limited access for the patient. Because the adjustments are often a daily task for the patient, easier access to the frame adjustment points would be a significant advantage.

In particular there is a need for a patient to receive feedback concerning the quantity of the actuation made in order to gain knowledge about the adjustment for each of the struts. Furthermore, there is a need for having an actuation member of a strut used to change the orientation of the fixation plates with respect to one another to be in a user-friendly position for the user.

BRIEF SUMMARY OF THE INVENTION

It is an object of the present invention to provide an external fixator system having an actuation unit which overcomes the drawback of prior art devices. In particular, the actuation unit preferably provides the user with a feedback concerning the quantity of actuation of the actuation unit.

Such an external fixator preferably comprises at least two fixation plates arranged at a distance to one another, and at least one adjustable length strut having a first end region and a second end region which are in connection with the at least two fixation plates and an at least one actuation unit to adjust a length of the at least one adjustable length strut in order to adjust a distance and/or orientation between the at least two fixation plates. The actuation unit is preferably in a fixed connection with at least one of the fixation plates as well as with at least one of the end regions of the respective strut in order to connect the strut with the fixation plate. Furthermore the actuation unit preferably comprises a feedback unit which provides a user with a feedback concerning the degree of the actuation.

The actuation unit preferably provides a gradual telescopic motion due to the arrangement of a feedback unit which is advantageous for the user. Due to the fixed connection with the fixation plate, it is possible to provide a very compact structure as the actuation unit can be arranged partly within the plate.

Preferably the actuation unit comprises a socket which is adapted to receive a tool to be actuated, whereby the socket is oriented such that it extends in or almost in direction of the strut and/or such that it extends perpendicular to a front surface of the fixation plate. This orientation has the advantage that the user gains very ergonomic access to actuate the actuation element. Hence this mechanism allows the effective length of the adjustable length strut to be adjusted from the top which allows easier patient access. This increases patient compliance—one of the significant challenges in deformity correction with an external fixator system.

Preferably the feedback unit provides the user with a haptic and/or an audible or acoustic and/or a visual feedback while the actuation unit is actuated.

Preferably the actuation unit comprises an outer sleeve with an opening and an actuation element which is arranged rotatable in the opening, wherein actuation unit is connected to the plates via parts of the outer sleeve.

The outer sleeve extends preferably into an opening which is arranged in the fixation plate, wherein the opening and the outer sleeve have a corresponding shape such that a relative rotation between the fixation plates is prevented.

Preferably the feedback unit comprises a spring-loaded ball which engages in one of a plurality of corresponding chambers such that upon a relative movement between the spring-loaded ball and the corresponding chambers the ball moves from an originating chamber to a neighboring chamber.

Preferably the feedback unit is arranged in connection with the outer sleeve and the actuation element.

Preferably the spring-loaded ball is arranged in an opening within the actuation element and the chambers are arranged within a bore hole or through opening of the outer sleeve, or the spring-loaded ball is arranged in an opening within the outer sleeve and wherein the chambers are arranged within the actuation element.

In a first aspect of the present invention, an external fixator system comprises at least two fixation plates each having upper and lower plate surfaces and each having a central axis that is perpendicular to the upper and lower plate surfaces, the at least two fixation plates being arranged at a distance and an angular orientation from one another. The external fixator system further comprises an actuation unit having proximal and distal end portions, the proximal end portion of the actuation unit being coupled to one of the at least two fixation plates such that at least a portion of an actuation element of the actuation unit is located proximally of the upper surface of the one of the at least two fixation plates, and at least one adjustable length strut having a first end region and a second end region coupled to two of the at least two fixation plates and the at least one actuation unit, the adjustable length strut having a threaded rod mechanically coupled to a distal end of the actuation element of the actuation unit. Preferably, actuation of the actuation element of the actuation unit rotates the threaded rod of the adjustable length strut such that the distance and angular orientation between the at least two fixation plates each changes based on an amount of the actuation.

In one embodiment of this first aspect of the present invention, the actuation unit includes an outer sleeve coupled to a through-hole of one of the at least two fixation plates such that the outer sleeve of the actuation unit is in a fixed connection with at least one of the at least two fixation plates. The outer sleeve preferably includes a bore hole in which at least a portion of a length of the actuation element of the actuation unit is rotatably received.

In another embodiment of this first aspect of the present invention, the through-hole of one of the at least two fixation plates and the outer sleeve of the actuation unit include corresponding outer surfaces having at least two different diameters such that relative rotation between the actuation unit and the one of the at least two fixation plates is prevented.

In yet another embodiment of this first aspect of the present invention, the actuation unit includes a socket adapted to receive a tool to provide the actuation of the actuation unit, the socket being oriented such that it extends perpendicular to a front surface of one of the at least two the fixation plates.

In still yet another embodiment of this first aspect of the present invention, the actuation unit includes a feedback unit such that upon actuation of the actuation unit a user is provided with visual, audible, and haptic feedback regarding the amount of the actuation. Preferably, the feedback unit includes a spring-loaded ball and a plurality of chambers adapted to house at least a portion of the spring-loaded ball therein such that upon actuation of the actuation unit a relative movement between the spring-loaded ball located in one of the plurality of chambers causes the spring-loaded ball to move from the one of the plurality of chambers to a neighbouring chamber. Preferably, the feedback unit is coupled to the outer sleeve and the actuation element of the actuation unit. Preferably, the spring-loaded ball of the feedback unit is arranged in an opening within the actuation element and the plurality of chambers are arranged within the bore hole of the outer sleeve. Preferably, the plurality of chambers are distributed in a regular spacing around perimeters of the bore hole of the outer sleeve and actuation element.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same.

A more complete appreciation of the subject matter of the present invention and the various advantages thereof can be realized by reference to the following detailed description in which reference is made to the accompanying drawings in which.

DETAILED DESCRIPTION

As used herein, when referring to the drill guides of the present invention, the term "proximal" means closer to the surgeon or in a direction toward the surgeon and the term "distal" means more distant from the surgeon or in a direction away from the surgeon. The term "anterior" means towards the front part of the body or the face and the term "posterior" means towards the back of the body. The term "medial" means toward the midline of the body and the term "lateral" means away from the midline of the body.

Referring to FIGS. 1-6, there is shown an embodiment of an external fixator system of the present invention. As shown in those figures, the external fixator system includes first and second fixation plates 1, 2 coupled to first and second bone segments L, F respectively, a plurality of adjustable length struts 3, at least one actuation unit 4, and a plurality of clamping units 4'.

Figure 1A:
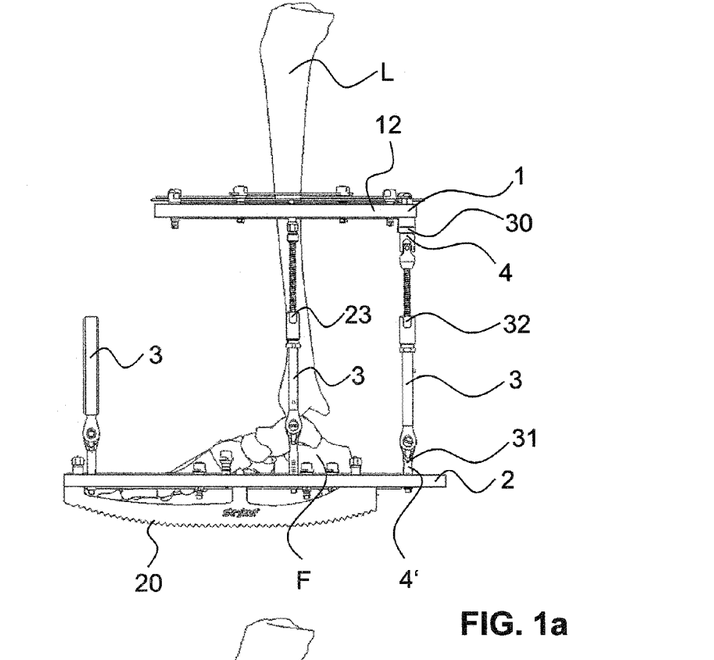
FIGS. 1a-c show side views of different strut configurations of an external fixator system of the present invention with first and second plates coupled to a tibia and a foot of a patient respectively.
Figure 1B:
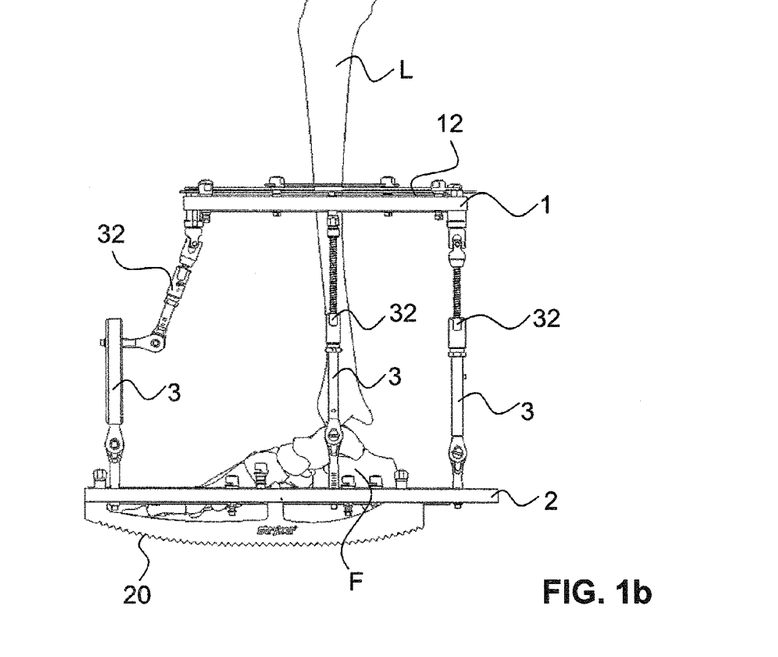
Figure 1C:
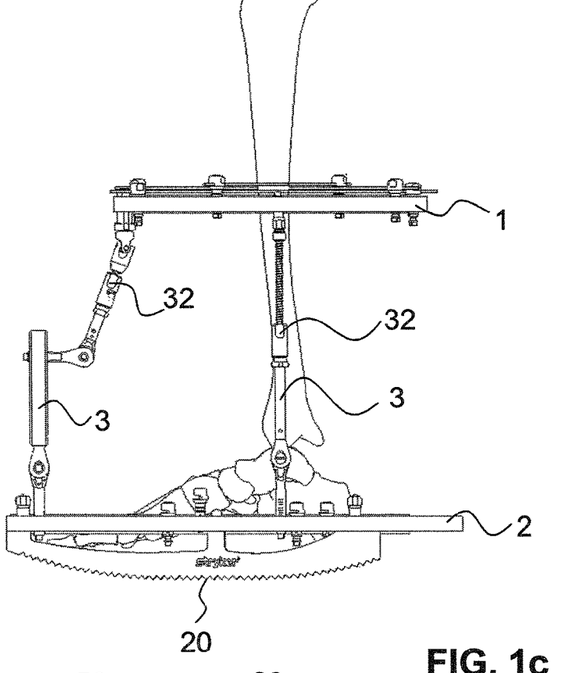

FIGS. 1a-c show an exemplary embodiment of an external fixator system. The external fixator system comprises at least two fixation plates 1, 2 which are arranged at a distance to each other and at least one adjustable length strut 3 which is in connection with the fixation plates 1, 2. Such struts are shown in U.S. Publications 2009/0198234 and 2009/0198235 the disclosures of which are incorporated herein by reference in their entirety. Fixation plates 1, 2 serve as bearing elements for pins which are in connection with bony structure such as first and second bone segments L, F, for example. The orientation as well as the distance between two fixation plates 1, 2 thereby define the orientation and distance between fractured elements of the bony structure. Each of the fixation plates 1, 2 comprises a front surface 12 which extends over the largest dimension of the plate 1, 2.

In the present embodiment there is an upper fixation plate 1 in connection with the lower leg L and a lower fixation plate 2 in connection with the foot F. The lower fixation plate 2 comprises also a rolling structure 20 to enable a user to walk around.

Adjustable length struts 3 each include a length-adjusting mechanism 32 having a threaded strut 33 and a non-rotating strut 34 having an internal thread along at least a portion of a length thereof in which the threaded strut 33 engages. Struts 3 include a first end region 30 and a second end region 31 in which the struts 3 are coupled to the respective fixation plates. In the present embodiment the struts 3 are connected to the upper fixation plate 1 by means of an actuation unit 4 and to the lower fixation plate 2 by means of a clamping element 4'. It is also possible to use an actuation unit 4 to connect the strut 3 to the upper fixation plate 1 as well as to the lower fixation plate 2. The actuation unit 4 is preferably provided to actuate the length-adjusting strut in order to adjust its length.

The actuation unit 4 is preferably in a fixed connection with fixation plates 1, 2 as shown in FIGS. 1a-c. The term fixed connection is to be understood as being a connection which prevents unintentional relative motion between the actuation unit 4 and fixation plates 1, 2. In particular, a rotational motion is preferably prevented. Preferably, fixation plates 1, 2 comprise a plurality of openings 10 in which such actuation units 4 can be arranged and such that the fixed connection can be established. The fixed connection has the advantage such that the device can be adjusted easily without the aid of several tools.

Figure 2:
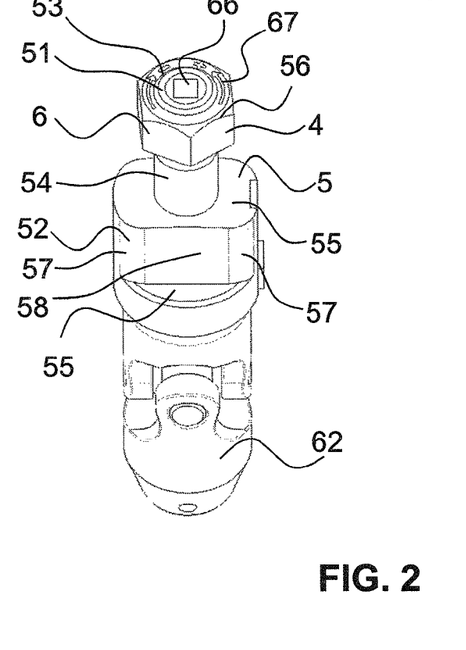
FIG. 2 shows an embodiment of an actuation unit of the present invention used in the external fixator system of FIGS. 1a-1c.
Figure 3:
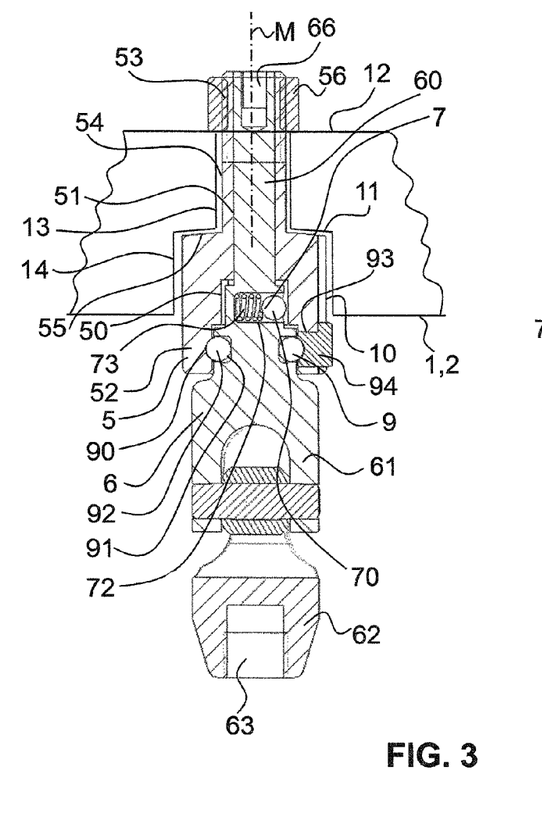
FIG. 3 shows a cross-sectional view of the actuation unit of FIG. 2.
Figure 4:
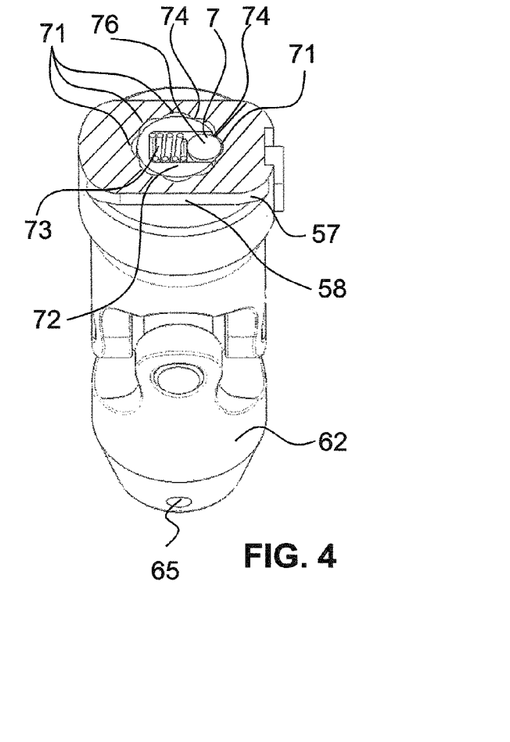
FIG. 4 shows a perspective partial cross-sectional view of the actuation unit of FIG. 3.

FIG. 2 shows the actuation unit 4 in a perspective view and FIGS. 3 and 4 show sectional views. The actuation unit 4 comprises an outer sleeve 5 in which an actuation element 6 is arranged. The actuation unit 4 is in connection with the fixation plate 1, 2 by means of the outer sleeve 5. Outer sleeve 5 is shown having a partly round configuration but may have other configurations such as rectangular, spherical, square and the like.

The outer sleeve 5 extends along a middle axis M as shown in FIG. 3 and comprises a through opening 50, a clamping section 51 and a bearing section 52. The clamping section 51 includes a threaded section 53 and a shaft section 54. The threaded section is in contact with a nut 56 which is used to secure the outer sleeve 5 to the fixation plate 1, 2. On the outer side a flange 55 divides the clamping section 51 from the bearing section 52. The bearing section 52 has mainly two purposes, namely to bear the 25 actuation element and to provide a bearing of the outer sleeve 5 in the opening 10. Hence the inner side provided by said through opening 50 serves to provide a bearing for an actuation element 6 of actuation unit 4. The outer side of the bearing section 52 serves mainly to provide a bearing for the outer sleeve 5 within said opening 10 in the ring 1 as explained below with regard to FIG. 3 in more detail. The outer side of the bearing section 52 has in the present 30 embodiment a rectangular cross-section with rounded edges 57 and flat sidewalls 58. Edges 57 and sidewalls 58 extend parallel to the middle axis M. The part which is located in vicinity of flange 55 however, is preferably also in connection with the opening in the fixation plate 1, 2.

In FIG. 3, one embodiment of an opening 10 in the fixation plate 1, 2 is schematically shown. The opening 10 comprises a shoulder 11 which subdivides the opening 10. The opening 10 comprises a first section 13 and a second section 14. The shoulder 11 is located between the first section 13 and the second section 14. The first section 13 of the opening 5 10 has therefore a complementary or corresponding shape as the shaft section 54. In the present embodiment shaft section 54 as well as first section 13 have circular cross-sections and the second section 14 as well as the bearing section 52 have a rectangular cross-section.

When the outer sleeve 5 is inserted into the opening 10 the shoulder 11 is preferably in contact with flange 55. The shaft section 54 of the outer sleeve 5 extends through the first section 13 of the opening 10 and the bearing section 52 extends into the section 14. The outer sleeve 5 is fixed to the fixation plate 1, 2 by means of nut 56 which retracts the outer sleeve 55 relative to fixation plate 1, 2 such that flange 55 comes in contact with the shoulder 11.

From FIG. 2 it becomes evident that the cross-section of the outer surface of the bearing section 52 which is in contact with the opening 10 is provided such that rotation of outer sleeve 5 relative to the fixation plate 1, 2 is prevented. For that reason the opining 10 has a complementary shape. In the present embodiment, the outer sleeve 5 has partly a rectangular cross-section with rounded edges. Here the rectangular cross-section is mainly provided by the outer side of the bearing section 52 or the outer surfaces of the bearing section 52, respectively.

The actuation element 6 of actuation unit 4 preferably extends along the middle axis M and comprises mainly a shaft section 60 which extends through the opening 50 of the outer sleeve and a connection section 61 which is in connection with strut 3. The actuation element 6 can be actuated, i.e. rotated, by means of a tool 67 shown in FIG. 5, which preferably engages in a socket 66 of the actuation element 6. Socket 66 is thereby arranged such that the tool can be introduced in a direction which is more or less in line with the axis of the strut or in a direction perpendicular to the fixation plate 1, 2, in particular to surface 12. The orientation of the socket 66 has thereby the advantage that easy access is provided from the top of the fixation system and that the length of the struts 3 can be adjusted easily by any user of the system.

Figure 5:
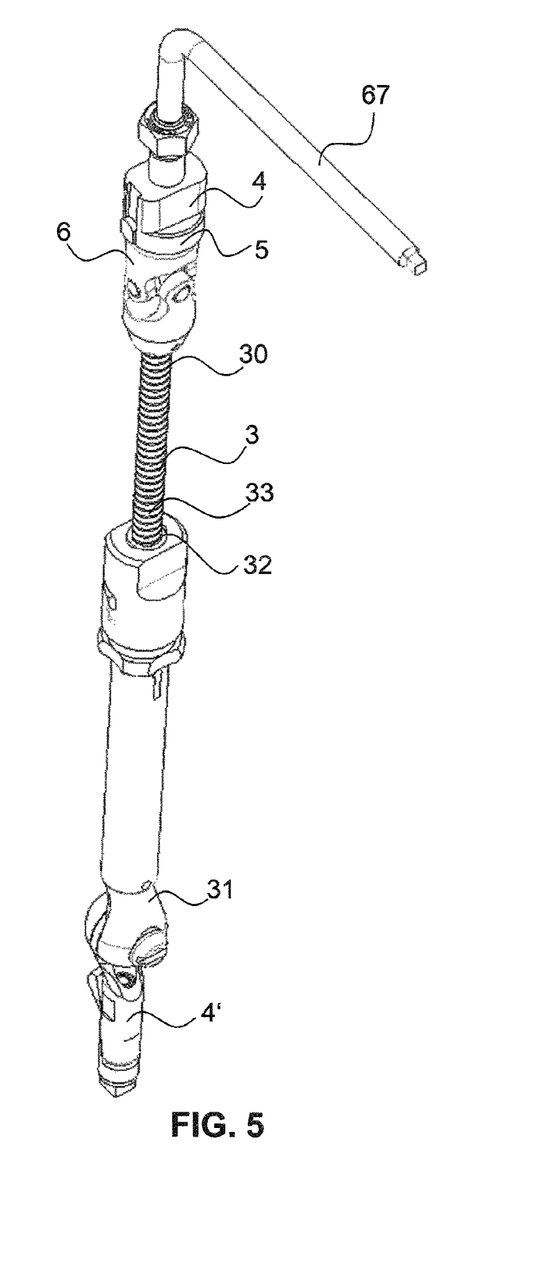
FIG. 5 shows the actuation unit of the previous figures in connection with an adjustable length strut to be used to connect two rings of the external fixator with each other.

The actuation element 6 is borne by means of a ball bearing 9 in the outer sleeve 5. In the present embodiment, the ball bearing 9 is provided by means of the shaft section 61 and the bearing section 52. A separate ball bearing is also possible, but a ball bearing which is provided according to the embodiment of FIG. 3 is preferably compact in terms of size.

As shown in FIG. 3, the bearing section 52 and the shaft section 61 preferably comprise respective grooves 90, 91 in which a plurality of balls 92 are arranged. Groove 90 extends into the surface of the opening 50 and encompasses the whole opening 50, whereas groove 91 is arranged in the shaft 61 of the actuation element 6. The grooves 90, 91 provide a channel in which the balls 92 are arranged. Balls 92 may be introduced into the channel via an opening 93 in the shaft section 61 which is covered by means of a cover 94.

Between the outer sleeve 5 and the actuation element 6 there is arranged a feedback unit 7 as shown in FIGS. 3 and 4. In the present embodiment, the feedback unit 7 is provided by means of a spring-loaded ball 70 and corresponding chambers 71. The spring-loaded ball 70 is arranged in an opening 72 in the actuation element 6. Between the ground of the opening 72 and the spring-loaded ball 70 there is arranged a spring 73 which provides a force that pushes the ball 70 into a respective chamber 71. The chambers 71 are arranged in the surface of the through opening 50 in the outer sleeve 5. Upon rotation of the actuation element 6 relative to the outer sleeve 5, the spring-loaded ball 70 is pushed against the spring force by means of the transition portion 74 between two neighboring chambers 71. As soon as the next chamber 71 is in line with the spring axis, the spring-loaded ball 70 will be moved into the respective chamber 71. This mechanism results in a clicking noise which provides the user with a respective audible feedback about the amount of actuation that is being made.

There are a plurality of chambers 71 arranged which are preferably distributed evenly around the perimeter of the through opening 50 of the outer sleeve 5. In the present embodiment, eight chambers 71 are arranged such that each chamber is located approximately 45° from a neighboring chamber, but it is also possible to arrange more or less than eight chambers. The number of chambers preferably depends on the application. Preferably, each time the actuation element is rotated such that the spring-loaded ball moves from one chamber 71 and into a neighboring chamber 71, adjustable length strut is lengthened 1 mm. Each time the actuation element is rotated such that the spring-loaded ball moves from one chamber 71 and into a neighboring chamber 71, adjustable length strut may be lengthened between 0.1 mm to 1 mm.

It is important for the adjustable length strut to not be lengthened so easily or inadvertently such that accidental injury may be caused. Osteogenesis generally occurs over a considerable length of time and lengthening and/or angulation adjustment between adjacent bone fragments should only be done in a prescribed manner. Therefore, chambers 71 are preferably deep enough to securely house at least a portion of the spring loaded ball 70 and a spring constant k of the spring is sufficient enough to force the ball against side walls in the respective chambers such that preferably only intended actuation of the actuation unit causes the actuation unit to actuate.

With regard to the embodiment as shown in FIGS. 3 and 4, opening 72 can also be arranged in the outer sleeve 5 and that the chambers 71 can also be arranged in the actuation element 6. With such a configuration a same or similar result can preferably be achieved.

Figure 6:
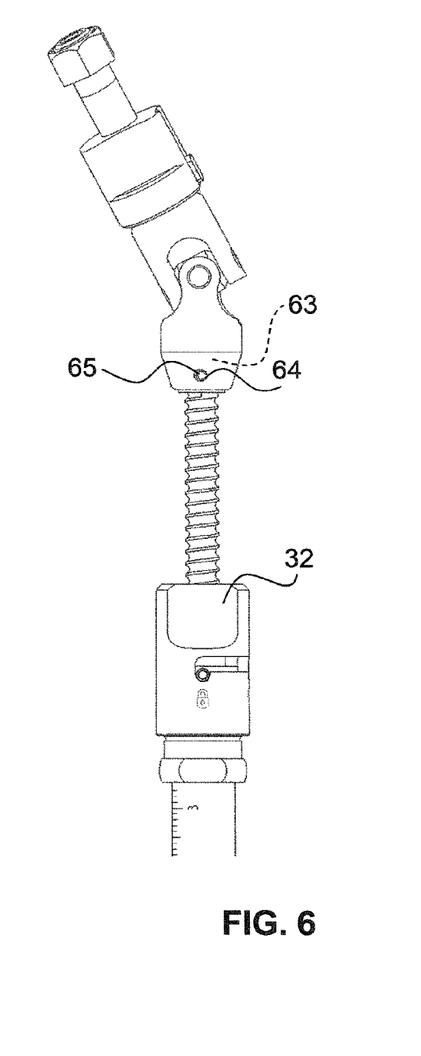
FIG. 6 shows a detailed view of FIG. 5.

The strut 3 with its end region is in a fixed connection with the actuation element 6. In the present embodiment, there is a cardan joint 62 arranged between the strut 3 and the actuation element 6 in order to compensate angular differences between the strut 3 and the actuation element 6. Furthermore the actuation element 6 comprises an opening 63 in which the strut 3 extends as shown in FIG. 6. Preferably the strut 3 is in connection with the opening 63 by means of a thread, a press fit or any other suitable connection method which prevents a relative movement between the strut 3 and the actuation element 6. In case a thread is used, it is advantageous to secure the thread by means of a pin 64 which extends through the opening 63 and the strut 3. For that reason a pin opening 65 is arranged in the region of the opening 63. The use of a cardan joint 62 has the advantage that adjustments can be made in advantageous manner, namely in a preferably precise and smooth manner.

Upon rotation of the actuation element 6, the strut will also be rotated and its length will be adjusted according to the degree of rotation. The feedback unit 7 then provides the user with an acoustic as well as with a haptic feedback due to its mechanical structure as outlined above.

The arrangement of the feedback unit 7 as mentioned herein has the advantage that in terms of dimension a very compact structure can be achieved. Thereby the overall-weight can be significantly reduced and it is preferably more convenient for the patient to use such a structure.

AS shown in FIG. 2, markings 67 showing the direction of rotation are arranged on an outer face of actuation unit 4 in order to allow the user to know in which direction actuation unit 4 is being actuated. In this region it is also possible to arrange a scale on which the user can visually recognize the amount of rotation, whereby a visual feedback can be provided.

FIGS. 5 and 6 show the strut 3 in connection with actuation unit 4 by way of its first end region 31 and with the clamping element 4' via its second end region 32. The clamping element 4' clamps the strut 3 in fixed manner to the fixation plate 1, 2 which is not shown here. The actuation unit 4 is also in a fixed connection with the respective fixation plate, but the actuation element 6 which is arranged within the actuation unit 4 is rotatable relative to the actuation unit 4. A rotation of the actuation element 6 preferably results in a rotation of the threaded strut 33 and in connection with the non-rotating strut section 34 such that the length of the strut 3 will be adjusted.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An actuation unit configured to couple to a ring of an external fixation frame, the actuation unit for adjusting a length of a telescopic strut, the actuation unit comprising:
   a housing having a borehole and an outer surface configured to be disposed within a hole in the ring when the housing is coupled to the ring; and
   an actuator shaft at least partially received in the borehole of the housing, the actuator shaft having a first portion located proximally of an upper surface of the ring when the actuator shaft is coupled to the housing and a second portion protruding distally from the housing, the second portion coupled to a rotatable portion of the telescopic strut,
   wherein actuation of the first portion of the actuator shaft causes adjustment in the length of the telescopic strut;
   wherein the actuation unit includes a feedback unit positioned proximal to the telescopic strut such that actuation of the first portion of the actuator shaft provides a user with visual, audible, and haptic feedback regarding an amount of the actuation.

2. The actuation unit of claim 1, wherein the housing of the actuation unit is fixedly connected with the hole in the ring when the housing is coupled to the ring.

3. The actuation unit of claim 2, wherein the actuator shaft is rotatably coupled to the housing.

4. The actuation unit of claim 1, wherein the actuation unit includes a socket adapted to receive a tool to provide the actuation of the first portion of the actuator shaft.

5. The actuation unit of claim 4, wherein the socket is oriented such that it extends perpendicular to a top surface of the ring.

6. The actuation unit of claim 1, wherein the feedback unit includes a spring-loaded ball and a plurality of chambers adapted to house at least a portion of the spring-loaded ball therein such that upon actuation of the first portion of the actuator shaft a relative movement between the spring-loaded ball located in one of the plurality of chambers causes the spring-loaded ball to move from the one of the plurality of chambers to a neighbouring chamber.

7. The actuation unit of claim 6, wherein the spring-loaded ball of the feedback unit is arranged in an opening within the actuator shaft and the plurality of chambers are arranged within the bore hole of the housing.

8. The actuation unit of claim 7, wherein the plurality of chambers are distributed in a regular spacing around perimeters of the bore hole of the housing and the actuator shaft.

9. The actuation unit of claim 1, wherein the feedback unit is coupled to the housing and the actuator shaft of the actuation unit.

10. An actuation unit of an adjustable length strut configured to couple to a ring of an external fixation frame, the actuation unit comprising:
   a housing having an outer surface configured to be disposed within a hole in the ring when the housing is coupled to the ring, the housing having a borehole; and
   an actuator shaft at least partially received in the borehole of the housing, the actuator shaft having a first portion and a second portion, the first portion at least partially located proximally of an upper surface of the ring when the actuator shaft is coupled to the housing, the second portion coupled to a threaded rod of the adjustable length strut,
   wherein actuation of the first portion of the actuator shaft causes adjustment in the length of the adjustable length strut;

wherein the actuation unit includes a feedback unit positioned proximal to the threaded rod such that actuation of the first portion of the actuator shaft provides a user with visual, audible, and haptic feedback regarding an amount of the actuation.

11. The actuation unit of claim 10, wherein the housing of the actuation unit is fixedly connected with the hole in the ring when the housing is coupled to the ring.

12. The actuation unit of claim 11, wherein the actuator shaft is rotatably coupled to the housing.

13. The actuation unit of claim 10, wherein the actuation unit includes a socket adapted to receive a tool to provide the actuation of the first portion of the actuator shaft.

14. The actuation unit of claim 13, wherein the socket is oriented such that it extends perpendicular to a top surface of the ring.

15. The actuation unit of claim 10, wherein the feedback unit includes a spring-loaded ball and a plurality of chambers adapted to house at least a portion of the spring-loaded ball therein such that upon actuation of the first portion of the actuator shaft a relative movement between the spring-loaded ball located in one of the plurality of chambers causes the spring-loaded ball to move from the one of the plurality of chambers to a neighbouring chamber.

16. The actuation unit of claim 15, wherein the spring-loaded ball of the feedback unit is arranged in an opening within the actuator shaft and the plurality of chambers are arranged within the bore hole of the housing.

17. The actuation unit of claim 16, wherein the plurality of chambers are distributed in a regular spacing around perimeters of the bore hole of the housing and the actuator shaft.

18. The actuation unit of claim 10, wherein the feedback unit is coupled to the housing and the actuator shaft of the actuation unit.

19. An actuation unit of an adjustable length strut configured to couple to a ring of an external fixation frame, the actuation unit comprising:
   a housing having an outer surface configured to be disposed within a hole in the ring when the housing is coupled to the ring, the housing having a borehole; and
   an actuator shaft at least partially received in the borehole of the housing, the actuator shaft having a first portion and a second portion, the first portion at least partially located proximally of an upper surface of the ring when the actuator shaft is coupled to the housing, the second portion coupled to a threaded rod of the adjustable length strut,
   wherein actuation of the first portion of the actuator shaft causes actuation of the second portion of the actuator shaft coupled to the threaded rod of the adjustable length strut, the actuation causing adjustment in the length of the adjustable length strut,
   wherein the actuation unit includes a feedback unit positioned proximal to the threaded rod such that actuation of the first portion of the actuator shaft provides a user with visual, audible, and haptic feedback regarding an amount of the actuation.

* * * * *